United States Patent [19]

Ishikawa et al.

[11] Patent Number: 4,814,337
[45] Date of Patent: Mar. 21, 1989

[54] DIHALOGEN-SUBSTITUTED THIOCYANOPYRIMIDINE DERIVATIVES, AND AGRICULTURAL AND HORTICULTURAL FUNGICIDAL COMPOSITIONS CONTAINING SAME

[75] Inventors: Katsutoshi Ishikawa, Kanagawa; Hitoshi Shimotori, Yokohama; Noboru Iida, Kanagawa; Toshiaki Kuwatsuka, Yokohama; Junya Fujiwara; Yuji Yanase, both of Kamakura; Takeshi Sekino, Hiratsuka, all of Japan

[73] Assignee: Mitsui Toatsu Chemicals, Incorporated, Tokyo, Japan

[21] Appl. No.: 38,895

[22] Filed: Apr. 16, 1987

[30] Foreign Application Priority Data

Apr. 28, 1986 [JP] Japan .................................. 61-96654

[51] Int. Cl.$^4$ .................... A01N 43/54; C07D 239/24
[52] U.S. Cl. ........................................ 514/269; 71/92; 544/319
[58] Field of Search .............. 544/319; 71/92; 558/10; 514/269

[56] References Cited

U.S. PATENT DOCUMENTS

| | | | |
|---|---|---|---|
| 2,642,353 | 8/1951 | Mowry et al. | 558/10 |
| 3,975,384 | 8/1976 | Narr et al. | 544/58.2 |
| 4,540,698 | 9/1985 | Ishikawa et al. | 514/270 |
| 4,648,896 | 3/1987 | Brunner | 544/319 |
| 4,652,569 | 3/1987 | Ishikawa et al. | 514/269 |

FOREIGN PATENT DOCUMENTS

| | | | |
|---|---|---|---|
| 0021939 | 10/1980 | European Pat. Off. | 544/319 |
| 1182584 | 2/1967 | United Kingdom | 544/319 |

OTHER PUBLICATIONS

Yakugaka Zasshi (The Journal of the Pharmacological Society of Japan), vol. 83, 1086, (1963; Kinugawa et al.; Chem. Abst., vol. 60, 8061–8062).
Razavi, Chem. Abst., vol. 72, 3499s.
Chem. Abstr., No. 64, 15896h; vol. 72, 3499s & 66891j; vol. 73, 3882g; vol. 76, 46212t; vol. 78, 97696c; vol. 79, 137181k; vol. 89, 101721d; vol. 90, 54968y.

*Primary Examiner*—Mary C. Lee
*Assistant Examiner*—Zinna Northington
*Attorney, Agent, or Firm*—Oblon, Fisher, Spivak, McClelland & Maier

[57] ABSTRACT

Disclosed are dihalogenothiocyanopyrimidine derivatives of the general formula

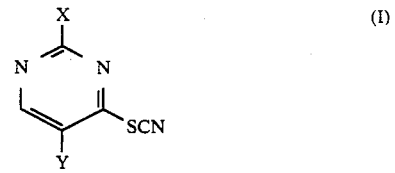

wherein X and Y are halogen atoms, a process for preparing such derivatives, as well as agricultural and horticultural fungicidal compositions containing such a derivative as active ingredient.

4 Claims, No Drawings

DIHALOGEN-SUBSTITUTED THIOCYANOPYRIMIDINE DERIVATIVES, AND AGRICULTURAL AND HORTICULTURAL FUNGICIDAL COMPOSITIONS CONTAINING SAME

TECHNICAL FIELD

This invention relates to dihalogenothiocyanopyrimidine derivatives of the general formula

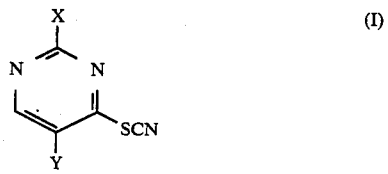

wherein X and Y are halogen atoms, a process for preparing such derivatives, as well as agricultural and horticultural fungicidal compositions containing such a derivative as active ingredient.

BACKGROUND ART

In the past, a large number of studies on pyrimidine derivatives have been made, an immense number of compounds have been synthesized, and numerous compounds having characteristic physiological activities have been found in the fields of agriculture and medicine. However, it is not yet known that a compound having a thiocyano group introduced into the pyrimidine nucleus has been put to practical use. Very few pyrimidine derivatives having a thiocyano group have been synthesized and little is known about their biological activities. Only one instance of research on thiocyanopyrimidine derivatives and their in vitro antimicrobial activities is reported in the Journal of the Pharmacological Society of Japan, 83, 1086 (1963). This report describes 15 thiocyanopyrimidine derivatives and their antimicrobial activities, and states that the most active compound is 2(or 4)-chloro-6-methyl-4(or 2)-thiocyanopyrimidine and the antimicrobial activities of thiocyanopyrimidine derivatives having a substituent at the 5-position tend to be lower. Nothing is known about thiocyanopyrimidine derivatives having a halogen atom at the 5-position.

The present inventors have already applied for a patent on an invention concerning thiocyanopyrimidine derivatives (see Japanese Patent Laid-Open No. 193970/'85). More specifically, this invention relates to 2,4-dihalogeno-5-alkylthio-6-thiocyanopyrimidine derivatives which are useful as agricultural and horticultural fungicides, and these compounds have a fairly powerful effect. However, they are disadvantageous in that their effect does not last long enough. Meanwhile, plant pathogens have a very great influence on agricultural and horticultural production. In recent years, the availability of a variety of fungicides for diverse plant diseases has enabled a certain degree of stable production, but much yet remains to be improved.

For example, in order to control late blight, caused by algal fungi (of the class Phycomycetes), and downy mildew of various crop plants, currently available fungicides must be used in very large amounts. Moreover, their effect tends to be influenced by the time of application, the weather, and the like, and cannot be regarded as stable. Furthermore, in the case of grey mold (caused by *Botrytis cinerea*), stem not (Sclerotinia Sclerotiorum) and like diseases of various crop plants, the development of resistance has made benzimidazole type or dicarboxylic acid imide type fungicides practically ineffective.

SUMMARY OF THE INVENTION

In order to solve the above-described problems, the present inventors made an intensive study of pyrimidine derivatives with their attention focused on the pyrimidine nucleus which is considered to play a special role in their interaction with the biological system.

As a result, the present inventors have discovered that, although it is described in the literature that thiocyanopyrimidine derivatives having a substituent at the 5-position exhibit a reduced antimicrobial activity, 2,5-dihalogeno-4-thiocyanopyrimidines having a halogen atom at the 5-position have a very powerful controlling effect on late blight and many other plant diseases caused by plant pathogens, that the halogen atom located at the 5-position serves to augment their effect, and that they exhibit a prolonged duration of action as compared with the 4-thiocyanopyrimidine derivatives having a methylthio group at the 5-position as described in the aforementioned Japanese Patent Laid-Open No. 193970/'85. The present invention has been completed on the basis of this discovery.

It is an object of the present invention to provide novel thiocyanopyrimidine derivatives.

It is anohher object of the present invention to provide a process for preparing such thiocyanopyrimidine derivatives.

It is still another object of the present invention to provide novel agricultural and horticultural fungicidal compositions involving a new mechanism of action in that they have a controlling effect on a wide variety of plant diseases including, in particular, late blight, downy mildew, grey mold and like diseases which cause great economic losses, they are likely to be effective against pathogenic fungi resistant to conventional fungicides, and their effect lasts long.

The above objects of the present invention are accomplished by providing, as novel compounds, dihalogenothiocyanopyrimidine derivatives of the general formula

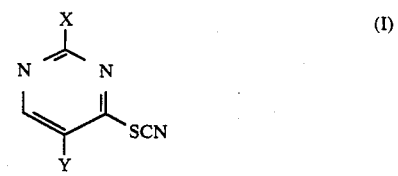

wherein X and Y are halogen atoms; a process for preparing dihalogenothiocyanopyrimidine derivatives of the general formula (I) which comprises reacting a trihalogenopyrimidine derivative of the general formula

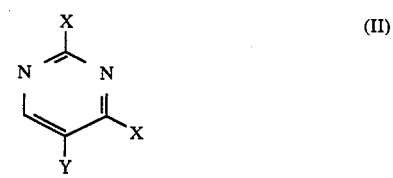

wherein X and Y are halogen atoms, with a thiocyanate of the general formula

MSCN                                            (III)

wherein M is an alkali metal or ammonium; and agricultural and horticultural fungicidal compositions containing a dihalogenothiocyanopyrimidine derivative of the general formula (I) as active ingredient.

DETAILED DESCRIPTION AND PREFERRED EMBODIMENTS OF THE INVENTION

The dihalogenothiocyanopyrimidine derivatives of the general formula (I), with which the present invention is concerned, include 2,5-difluoro-4-thiocyanopyrimidine, 5-chloro-2-fluoro-4-thiocyanopyrimidine, 5-bromo-2-fluoro-4-thiocyanopyrimidine, 2-fluoro-5-iodo-4-thiocyanopyrimidine, 2-chloro-5-fluoro-4-thiocyanopyrimidine, 2,5-dichloro-4-thiocyanopyrimidine, 5-bromo-2-chloro-4-thiocyanopyrimidine, 2-chloro-5-iodo-4-thiocyanopyrimidine, 2-bromo-5-fluoro-4-thiocyanopyrimidine, 2-bromo-5-chloro-4-thiocyanopyrimidine, 2,5-dibromo-4-thiocyanopyrimidine, 2-bromo-5-iodo-4-thiocyanopyrimidine, 5-fluoro-2-iodo-4-thiocyanopyrimidine, 5-chloro-2-iodo-4-thiocyanopyrimidine, 5-bromo-2-iodo-4-thiocyanopyrimidine, and 2,5-diiodo-4-thiocyanopyrimidine.

The dihalogenothiocyanopyrimidine derivatives of the general formula (I) in accordance with the present invention are novel compounds and useful because of their excellent controlling effect on a wide variety of plant diseases including late blight, downy mildew, powdery mildew, grey mold and like diseases of various crop plants. Moreover, they are quite safe for the crop plants and exhibit no phytotoxicity to, for example, tomatoes, cucumbers, potatoes and the like. Furthermore, their toxicity to animals is also low.

Now, the process for preparing dihalogenothiocyanopyrimidine derivatives of the general formula (I) in accordance with the present invention will be described hereinbelow. The compounds of the present invention can be prepared according to the following equation:

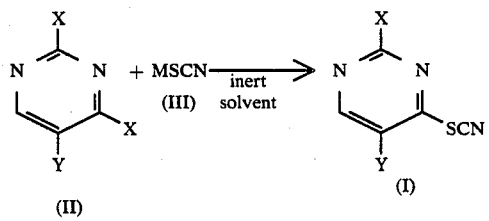

Among various trihalogeno compounds of the general formula (II) useful as starting materials, dichloro compounds of the general formula (II) in which X is chlorine can be obtained by treating a 5-halogenouracil with phosphorus oxychloride in the presence of dimethylaniline, and dibromo compounds of the general formula (II) in which X is bromine can be obtained by treating a 5-halogenouracil with phosphorus oxybromide in the presence of dimethylaniline. Further, diiodo compounds of the general formula (II) in which X is iodine can be obtained by treating a dichloro compound with concentrated hydriodic acid, and difluoro compounds of the general formula (II) in which X is fluorine can be obtained by treating a dichloro compound with potassium fluoride.

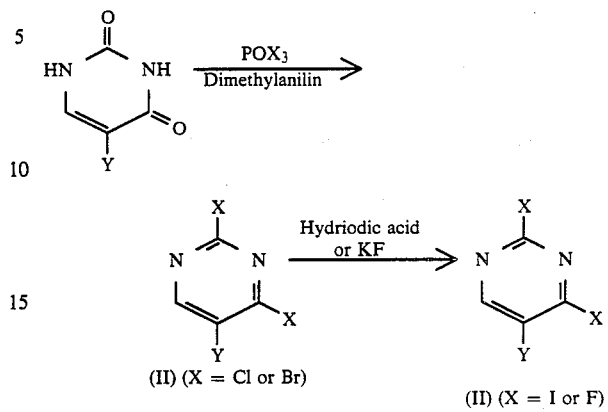

Now, the process for preparing 2,5-dihalogeno-4-thiocyanopyrimidines (I) in accordance with the present invention will be described in greater detail. This process comprises reacting a trihalogeno compound (II) with a thiocyanate (III), preferably in a solvent. Useful thiocyanates include potassium thiocyanate, sodium thiocyanate, ammonium thiocyanate and the like, and any of them can produce good results. It is the type of solvent used that has the greatest influence on the reaction of the present invention. If the reaction is carried out in an alcohol such as methanol, ethanol or the like, the reaction rate will be low even under refluxed conditions. Moreover, a resinous material will be formed as a by-product, resulting in a very low yield. If the reaction is carried out in an aprotic solvent such as acetone, dimethyl sulfoxide, N,N-dimethylformamide, 1,3-dimethyl-2-imidazolidinone or the like, by-products having two thiocyano groups or isothiocyanates resulting from the rearrangement of the thiocyano group will be formed, so that the desired product (I) will be obtained only in low yield. However, it has surprisingly been found that, in contrast to the cases where the aforesaid solvents are used, the yield can be markedly enhanced by carrying out the reaction in an organic acid such as formic acid, acetic acid, propionic acid or the like. The reactivities in formic acid, acetic acid and propionic acid decrease in the order mentioned, and the effect of formic acid is especially marked. For example, it takes 5 hours or more to complete the reaction when it is carried out in acetic acid at 50° C., whereas the reaction is completed within an hour when it is carried out in formic acid at the same temperature. Although the reaction temperature can range from 10° C. to the boiling point of the solvent, a reaction temperature within the range of 20 to 60° C. should preferably be employed so as to minimize the formation of by-products and ensure a reasonable reaction time. Thus, it may safely be said that, judging from both the selectivity of the reaction and the rapidity of its progress, formic acid exhibits very excellent properties in the reaction of the present invention, as contrasted strikingly with other organic solvents and, in particular, other organic acids having relatively good properties.

After completion of the reaction, the reaction mixture is poured into a large volume of water. Where a solid precipitate separates out, it may be collected by filtration and then dried. Thus, there can be obtained crude crystals of the desired product in a 90% or higher yield. Where an oily material separates out, it may be extracted with an inert solvent (such as ethyl acetate, benzene, toluene or the like), washed with water, and then dehydrated to obtain a crude oil. The crude product itself has a relatively high purity and may be used as a fungicide without further purification. However, if necessary, a pure product can be obtained by recrystallization from any of commonly used solvents such as isopropyl ether, chloroform, carbon tetrachloride, ethyl acetate, ethanol, methanol and the like, or by column chromatography.

The compounds of the present invention have a powerful controlling effect on a wide variety of plant diseases including late blight, downy mildew, powdery mildew, grey mold and like diseases of various crop plants.

The compounds of the present invention may be applied by various methods including disinfection of seeds, spraying over stems and leaves, treatment of soil, and the like, and any of the application methods commonly used by those skilled in the art permits them to exhibit their effectiveness to the fullest extent. The amount and concentration at which the compounds of the present invention are applied may vary according to the crop plant to be treated, the disease to be controlled, the extent of damage by the disease, the type of formulation, the method of application, various environmental conditions and the like. In case of spraying, it is suitable to use them in an amount of 2 to 200 g per are and preferably 5 to 100 g per are. The concentration of the sprayed suspension is suitably within the range of 100 to 1,000 ppm and preferably 200 to 500 ppm.

The agricultural and horticultural fungicidal compositions of the present invention cannot only be used in admixture with agricultural chemicals (such as other fungicides, insecticides, herbicides, plant growth regulators, etc.), soil conditioners and/or fertilizing materials, but also be combined with them to form mixed preparations.

Although the compounds of the present invention may be applied as such, they are preferably applied in the form of compositions prepared by mixing them with carriers including solid or liquid diluents. The term "carrier" as used herein means any synthetic or natural, inorganic or organic material that can be used to assist the active ingredient in reaching the sites to be treated or to facilitate the storage, transport and handling of the compound used as active ingredient.

Suitable solid carriers include inorganic materials such as clays (e.g., montmorillonite, kaolinite, etc.), diatomaceous earth, china clay, talc, vermiculite, gypsum, calcium carbonate, silica gel, ammonium sulfate, etc.; organic materials of vegetable origin, such as soybean meal, sawdust, flour, etc.; urea; and the like.

Suitable liquid carriers include aromatic hydrocarbons such as toluene, xylene, cumene, etc.; paraffinic hydrocarbons such as kerosine, mineral oil, etc.; halogenated hydrocarbons such as carbon tetrachloride, chloroform, dichloroethane, etc.; ketones such as acetone, methyl ethyl ketone, etc.; ethers such as dioxane, tetrahydrofuran, etc.; alcohols such as methanol, propanol, ethylene glycol, etc.; dimethylformamide; dimethyl sulfoxide; water; and the like.

In order to further augment the effectiveness of the compounds of the present invention, the following adjuvants may be used, alone or in combination, according to the intended purpose and in consideration of the type of formulation, the conditions of application, etc.

For purposes of emulsification, dispersion, spreading, wetting, binding, stabilization and the like, there may be used water-soluble bases such as lignin sulfonates, etc.; anionic surface active agents such as alkylbenzenesulfonates, etc.; nonionic surface active agents such as alkylsulfuric esters, polyoxyalkylene alkyl ethers, polyoxyalkylene alkylaryl ethers, polyoxyalkylene alkyl amines, polyoxyalkylene alkyl amides, polyoxyalkylene alkyl thioethers, polyoxyalkylene fatty acid esters, glycerol fatty acid esters, sorbitan fatty acid esters, polyoxyalkylene sorbitan fatty acid esters, polyoxypropylene-polyoxyethylene block copolymer, etc.; lubricants such as calcium stearate, wax, etc.; stabilizers such as isopropyl hydrogen phosphate, etc.; and other adjuvants such as methyl cellulose, carboxymethyl cellulose, casein, gum arabic, etc.

However, it is to be understood that useful adjuvants are not limited to the foregoing.

In the compositions containing a compound of the present invention, the active ingredient is usually present in an amount of 0.5 to 20% by weight for dusts, 5 to 30% by weight for emulsifiable concentrates, 10 to 90% by weight for wettable powders, 0.1 to 20% by weight for granules, or 10 to 90% by weight for flowable formulations.

Now, the process for preparing the compounds of the present invention is more specifically explained with reference to the following Synthesis Examples.

Synthesis Example 1

Synthesis of 2 chloro-5-iodo-4-thiocyanopyrimidine (Compound No. 1)

Into a 300-ml four-necked flask fitted with a thermometer and a stirrer were charged 35.0 g of 2,4-dichloro-5-iodopyrimidine, 15.0 g of potassium thiocyanate, and 150 ml of formic acid. This reaction mixture was stirred at room temperature (20° C.) for 3 hours. After completion of the reaction, the reaction mixture was poured into a large volume of water and the resulting precipitate was filtered off and dried to obtain crude crystals. Then, these crystals were recrystallized from toluene to obtain 28.5 g (75.4% yield) of 2-chloro-5-iodo-4-thiocyanopyrimidine, m.p. 185°–186.5° C.

NMR (CCl$_4$): $\delta$=8.34 ppm (s).
IR (KBr): 2190 cm$^{-1}$ (—SCN).

SYNTHESIS EXAMPLE 2

Synthesis of 2-chloro 5-fluoro-4-thiocyanopyrimidine (Compound No. 2)

In 50 ml of formic acid, a reaction of 10.0 g of 2,4-dichloro-5-fluoropyrimidine and 5.8 g of potassium thiocyanate was conducted at room temperature (20° C.) for 5 hours in a similar manner as Synthesis Example 1. Then, the reaction mixture was treated in a similar procedure as Synthesis Example 1, there was obtained a 68.0% yield of 2-chloro-5-fluoro-4-thiocyanopyrimidine, m.p. 103°–104° C.

NMR (DMSO-d$_6$) $\delta$=8.85 ppm (s).
IR (KBr): 2180 cm$^{-1}$ (—SCN)

SYNTHESIS EXAMPLE 3

Synthesis of 2,5-dichloro-4-thiocyanopyrimidine (Compound No. 3)

In 100 ml of formic acid, a reaction of 17.0 g of 2,4,6-trichloropyrimidine and 9.7 g of potassium thiocyanate was conducted at room temperature (20° C.) for 4 hours in a similar manner as Synthesis Example 1. Then, the reaction mixture was treated in a similar procedure as Synthesis Example 1, there was obtained a 65.0% yield of 2,5-dichloro-4-thiocyanopyrimidine, m.p. 160.5°–161.5° C.

NMR (DMSO-$d_6$): $\delta$=8.85 ppm (s).
IR (KBr): 2160 cm$^{-1}$ (—SCN)

SYNTHESIS EXAMPLE 4

Synthesis of 5-bromo-2-chloro-4-thiocyanopyrimidine (Compound No. 4)

In 100 ml of formid acid, a reaction of 23.0 g of 5-bromo-2,4-dichloropyrimidine and 10.0 g of potassium thiocyanate was conducted at room temperature (20° C.) for 4 hours in a similar manner as Synthesis Example 1. Then, the reaction mixture was treated in a similar procedure as Synthesis Example 1, there was obtained a 80.0% yield of 5-bromo-2-chloro-4-thiocyanopyrimidine, m.p. 166.5°–170° C.

NMR (DMSO-$d_6$): $\delta$=8.85 ppm (s).
IR (KBr): 2150 cm$^{-1}$ (—SCN)

SYNTHESIS EXAMPLE 5

Synthesis of 5-chloro-2-iodo-4-thiocyanopyrimidine (Compound No. 5)

In 100 ml of formic acid, a reaction of 18.4 g of 5-chloro-2,4-diiodopyrimidine and 6.0 g of potassium thiocyanate was conducted at 60° C. for 1 hour in a similar manner as Synthesis Example 1. Then, the reaction mixture was treated in a similar procedure as Synthesis Example 1, there was obtained a 62.5% yield of 5-chloro-2-iodo-4-thiocyanopyrimidine, m.p. 183°–186° C.

IR (KBr): 2170 cm$^{-1}$ (—SCN)

The 5-chloro-2,4-diiodopyrimidine used as a starting material could readily be obtained by adding 2,4,5-trichloropyrimidine to hydriodic acid and stirring this mixture at room temperature for 4 hours.

SYNTHESIS EXAMPLE 6

Synthesis of 5-bromo-2-iodo-4-thiocyanopyrimidine (Compound No. 6)

In 30 ml of formic acid, a reaction of 4.11 g of 5-bromo-2,4-diiodopyrimidine and 1.17 g of potassium thiocyanate was conducted at room temperature (20° C.) for 5 hours in a similar manner as Synthesis Example 1. Then, the reaction mixture was treated in a similar procedure as Synthesis Example 1, there was obtained a 82.4% yield of 5-bromo-2-iodo-4 thiocyanopyrimidine, m.p. 199°–202° C.

IR (KBr): 2180 cm$^{-1}$ (—SCN)

SYNTHESIS EXAMPLE 7

Synthesis of 2,5-diodo-4-thiocyanopyrimidine (Compound No. 7)

In 150 ml of formic acid, a reaction of 19.0 g of 2,4,5-triiodopyrimidine and 5.0 g of potassium thiocyanate was conducted at room temperature (20° C.) for 3 hours in a similar manner as Synthesis Example 1. Then, the reaction mixture was treated in a similar procedure as Synthesis Example 1, there was obtained a 84.7% yield of 2,5-diiodo-4-thiocyanopyrimidine, m.p. 183°–185° C.

IR (KBr): 2160 cm$^{-1}$ (—SCN)

Next, the preparation of agricultural and horticultural fungicidal compositions in accordance with the present invention is more specifically explained with reference to the following Formulations. In these Formulations, the compound constituting the active ingredient is identified by the same number as used in the foregoing Synthesis Examples. All parts are by weight.

Formulation 1 (Wettable powder)

Thirty (30) parts of Compound No. 1, 44 parts of diatomaceous earth, 20 parts of clay, 1 part of sodium lignin sulfonate, and 2 parts of sodium alkylbenzenesulfonate were ground and intimately blended to obtain 100 parts of a wettable powder.

Formulation 2 (Granules)

Seven (7) parts of Compound No. 1, 1 part of polyethylene glycol nonylphenyl ether, 3 parts of polyvinyl alcohol, and 89 parts of clay were blended intimately. This blend was mixed with water, granulated and then dried to obtain 100 parts of granules.

Formulation 3 (Wettable powder)

Fifty (50) parts of Compound No. 1, 40 parts of talc, 5 parts of sodium lauryl phosphate, and 5 parts of sodium alkylnaphthalenesulfonate were blended to obtain 100 parts of a wettable powder.

Formulation 4 (Wettable powder)

Fifty (50) parts of Compound No. 2, 10 parts of sodium lignin sulfonate, 5 parts of sodium alkylnaphthalenesulfonate, 10 pats of white carbon, and 25 parts of diatomaceous earth were blended and then ground to obtain 100 parts of a wettable powder.

Formulation 5 (Flowable formulation)

Forty (40) parts of Compound No. 1, 3 parts of carboxymethyl cellulose, 2 parts of sodium lignin sulfonate, 1 part of dioctyl sulfosuccinate sodium salt, and 54 parts of water were wet ground in a sand grinder to obtain 100 parts of a flowable formulation.

Next, the effectiveness of the compounds of the present invention as agricultural and horticultural fungicides is illustrated by the following Tests. In these Tests, the compounds enumerated below were used as controls.

A: 2-Chloro-6-methyl-4-thiocyanopyrimidine.
B: Tetrachloroisophthalonitrile (Daconil).
C: 1-(Butylcarbamoyl)-2-benzimidazolylcarbamic acid
methyl ester (Benlate).
D: 2,4-Dichloro-5-methylthio-6-thiocyanopyrimidine.

Control Compound A is a compound as described in the aforementioned Journal of the Pharmacological Society of Japan, 83, 1086 (1963), B is a commercially available fungicide for the control of potato late blight, cucumber downy mildew and the like, C is a commercially available fungicide for the control of grey mold and the like, and D is a compound as described in Japanese Patent Laid-Open No. 193970/'85.

Test 1 [Control test for potato late blight (caused by Phytophthora infestans)]

In a greenhouse, potato plants (cultivar: Danshaku) were grown in pots until they reached a height of about 25 cm. Then, using a spray gun (1.0 kg/cm$^2$), a suspension of each test compound having a predetermined concentration (which had been formed by preparing a wettable powder according to the procedure of the above-described Formulation 3 and diluting it with water to the predetermined concentration) was sprayed in an amount of 50 ml per 3 pots, and airdried. After the pots were maintained in the greenhouse for 5 days, a zoospore suspension was prepared from the pathogenic fungus of potato late blight which had previously been cultured on potato slices for 7 days, and then sprayed over the potato plants treated with the respective test compounds. After the inoculated plants were maintained at a temperature of 17°–19° C. and a relative humidity of 95% or higher for 6 days, the degree of formation of spots infected was examined.

For each leaf, the relative spot area infected was evaluated by visual inspection, and the lesion index was determined on the basis of the following criteria.

Lesion index 0:  Relative spot area infected 0%
Lesion index 1:  Relative spot area infected 1–5%.
Lesion index 2:  Relative spot area infected 6–25%.
Lesion index 3:  Relative spot area infected 26–50%.
Lesion index 4:  Relative spot area infected 51% or larger.

Using the lesion indexes thus obtained, the lesion degree of each test group was calculated according to the following equation.

$$\text{Lesion degree} = \frac{4n_4 + 3n_3 + 2n_2 + 1n_1 + 0n_0}{N}$$

where
- $n_0$: the number of leaves having the lesion index of 0.
- $n_1$: the number of leaves having the lesion index of 1.
- $n_2$: the number of leaves having the lesion index of 2.
- $n_3$: the number of leaves having the lesion index of 3.
- $n_4$: the number of leaves having the lesion index of 4.
- $N = n_0 + n_1 + n_2 + n_3 + n_4$.

The results thus obtained are shown in Table 1.

TABLE 1
Results of Control Test for Potato Late Blight

| Test compound | Concentration of active ingredient | Lesion degree | Phytotoxicity |
|---|---|---|---|
| Compound No. 1 | 200 ppm | 0 | No |
| Compound No. 2 | " | 0.25 | " |
| Compound No. 3 | " | 0 | " |
| Compound No. 4 | " | 0 | " |
| Compound No. 5 | " | 0 | " |
| Compound No. 6 | " | 0 | " |
| Compound No. 7 | " | 0 | " |
| Control Compound A | " | 3.41 | " |
| Control Compound B | " | 1.60 | " |
| Control Compound C | " | 0.72 | " |
| No treatment | — | 3.77 | — |

Test 2 [Control test for cucumber plants downy mildew (caused by *Pseudoperonospora cubensis*)]

In a greenhouse, cucumber plants were grown in pots until they reached the two-leaf stage. Then, using a spray gun (1.0 kg/cm$^2$), a suspension of each test compound having a predetermined concentration (which had been formed by preparing a wettable powder according to the procedure of the above-described Formulation 3 and diluting it with water to the predetermined concentration) was sprayed in an amount of 30 ml per 3 pots, and air-dried. After . the pots were maintained in the greenhouse for 5 days, a spore suspension was prepared by collecting the pathogenic fungus of downy mildew from the spot regions of cucumber leaves affected by downy mildew and suspending it in desalted water, and then sprayed over the cucumber plants. Immediately after that, the inoculated plants were maintained at a temperature of 18°–20° C. and a relative humidity of 95% or higher for 24 hours, and then placed in the greenhouse (at 18°–27° C.). After 7 days, the degree of formation of spots was examined. The results thus obtained are shown in Table 2.

The criteria for evaluation and the method for expressing the severity of lesions were the same as described in Test 1.

TABLE 2
Results of Control Test for Cucumber Downy Mildew

| Test compound | Concentration of active ingredient | Lesion degree | Phytotoxicity |
|---|---|---|---|
| Compound No. 1 | 200 ppm | 0 | No |
| Compound No. 2 | " | 0.41 | " |
| Compound No. 3 | " | 0 | " |
| Compound No. 4 | " | 0 | " |
| Compound No. 5 | " | 0.13 | " |
| Compound No. 6 | " | 0 | " |
| Compound No. 7 | " | 0.18 | " |
| Control Compound A | " | 3.65 | " |
| Control Compound B | " | 1.68 | " |
| Control Compound D | " | 0.93 | " |
| No treatment | — | 3.45 | — |

Test 3 [Control test for cucumber grey mold (caused by *Botrytis cinerea*)]

In a greenhouse, cucumber plants (cultivar: Sagami-hanjiro) were grown in pots until they reached the cotyledon stage. Then, using a spray gun (1.0 kg/cm$^2$), a suspension of each test compound having a predetermined concentration (which had been formed by preparing a wettable powder according to the procedure of the above-described Formulation 3 and diluting it with water to the predetermined concentration) was sprayed in an amount of 20 ml per 3 pots, and air-dried. After the pots were maintained n the greenhouse for 5 days, a spore suspension was prepared from the pathogenic fungus of grey mold which had previously been culture in PDA medium, and then sprayed over the cucumber plants. Immediately after that, the inoculated plants were maintained at a temperature of 22°–24° C. and a relative humidity of 95% or higher for 5 days. Thereafter, the degree of formation of infected spots on the cotyledons was examined. The results thus obtained are shown in Table 3.

The criteria for evaluation were as follows:
Lesion index 0: Relative spot area infected 0%.
Lesion index 1: Relative spot area infected 1–10%.
Lesion index 2: Relative spot area infected 11–25%.
Lesion index 3: Relative spot area infected 26–50%.
Lesion index 4"Relative spot area infected 51% or larger.

For all cotyledons, the lesion index was determined on the basis of the above-described criteria, and the lesion degree of each test group was then calculated in the same manner as described in Test 1.

TABLE 3

Results of Control Test for Cucumber Grey Mold

| Test compound | Concentration of active ingredient | Lesion degree | Phytotoxicity |
| --- | --- | --- | --- |
| Compound No. 1 | 500 ppm | 0 | No |
| Compound No. 2 | " | 0 | " |
| Compound No. 3 | " | 0.34 | " |
| Compound No. 4 | " | 0.15 | " |
| Compound No. 5 | " | 0.26 | " |
| Compound No. 6 | " | 0.15 | " |
| Compound No. 7 | " | 0.38 | " |
| Control Compound A | " | 3.10 | " |
| Control Compound B | " | 1.41 | " |
| Control Compound D | " | 1.00 | " |
| No treatment | — | 4.00 | — |

Test 4 [Control test for tomato late blight (caused by *Phytophthora infestans*)]

In a greenhouse, tomato plants (cultivar: Sekaiichi) were grown in pots until they reached a height of about 25 cm. Then, using a spray gun (1.0 kg/cm$^2$), a suspension of each test compound having a predetermined concentration (which had been formed by preparing a wettable powder according to the procedure of the above described Formulation 3 and diluting it with water to the predetermined concentration) was sprayed in an amount of 50 ml per 3 pots, and air-dried. On the other hand, a zoospore suspension was prepared from the pathogenic fungus of tomato late blight which had previously been cultured on potato slices for 7 days, and then sprayed over the tomato plants treated with the respective test compounds. After the inoculatd plants were maintained at a temperature of 17°–19° C. and a relative humidity of 95% or higher for 6 days, the degree of formation of spots was examined.

The criteria for evaluation and the method for expressing the severity of lesions were the same as described in Test 1. The results thus obtained are shown in Table 4.

TABLE 4

Results of Control Test for Tomato Late Blight

| Test compound | Concentration of active ingredient | Lesion degree | Phytotoxicity |
| --- | --- | --- | --- |
| Compound No. 1 | 100 ppm | 0 | No |
| Compound No. 2 | " | 0 | " |
| Compound No. 3 | " | 0 | " |
| Compound No. 4 | " | 0 | " |
| Compound No. 5 | " | 0 | " |
| Compound No. 6 | " | 0 | " |
| Compound No. 7 | " | 0 | " |
| Control Compound B | " | 1.6 | " |
| Control Compound D | " | 0.5 | " |
| No treatment | — | 2.6 | — |

Test 5 [(Control test for wheat leaf rust (caused by *Puccinia recondita*)]

In a greenhouse, wheat plants (cultivar: Norin No. 6I) were grown in pots until they reached the five- or six-leaf stage. Then, using a spray gun (1.0 kg/cm$^2$), a suspension of each test compound having a predetermined concentration (which had been formed by preparing a wettable powder according to the procedure of the above-described Formulation 3 and diluting it with water to the predetermined concentration) was sprayed in an amount of 30 ml per 3 pots, and air-dried. These wheat plants were artificially inoculated with spores of the pathogenic fungus of wheat leaf rust. After the inoculated plants were maintained in the greenhouse for 10 days, the degree of formation of spots was examined. For each plant, the relative spot area was evaluated by visual inspection, and the lesion index was determined. Then, the lesion degree of each test group was calculated in the same manner as described in Test 1. The results thus obtained are shown in Table 5.

TABLE 5

Results of Control Test for Wheat Leaf Rust

| Test compound | Concentration of active ingredient | Lesion degree | Phytotoxicity |
| --- | --- | --- | --- |
| Compound No. 1 | 200 ppm | 0 | No |
| Compound No. 2 | " | 0.93 | " |
| Compound No. 3 | " | 0 | " |
| Compound No. 4 | " | 0 | " |
| Compound No. 5 | " | 0.50 | " |
| Compound No. 6 | " | 0 | " |
| Compound No. 7 | " | 0.37 | " |
| Control Compound A | " | 3.00 | " |
| Control Compound D | " | 1.53 | " |
| No treatment | — | 3.20 | — |

It is evident from the results of Tests 1 to 5 that the compounds of the present invention have a far more powerful controlling effect on quite different types of plant diseases including potato late blight, cucumber downy moldew, grey mold, and wheat leaf rust, as compared with commercially available fungicides heretofore in common use. It is also noted that, though having a somewhat similar chemical structure, 2-chloro-6-methyl-4-thiocyanopyrimidine as described in the aforementioned report is practically ineffective in controlling such plant diseases. Moreover, when compared with 2,4-dichloro-5-methylthio-6-thiocyanopyrimidine (Control Compound D) which is one of the compounds described in the specification of the previous patent application (Japanese Patent Laid-Open No. 193970/'85) of the present inventors, the compounds of the present invention exhibit a more powerful controlling effect and a far longer duration of action (as can be seen from the fact that an excellent controlling effect was observed even when a pathogen was inoculated 5 days after treatment with the compounds of the present invention). Thus, it is evident that the compounds of the present invention have excellent properties which cannot be predicted from any of the knowledge accumulated in the prior art.

It can be seen from the above description that, when compared with commercially available fungicides, the dihalogenothiocyanopyrimidine derivatives of the present invention have a more powerful controlling effect on a wide variety of plant diseases including quite different types of plant diseases such as potato late blight, cucumber downy mildew, grey mold and wheat leaf rust, and their effect lasts far longer. Thus, they are obviously useful as agricultural and horticultual fungicides.

In the process for preparing the dihalogenothiocyanopyrimidine derivatives of the present invention, the introduction of a thiocyano group by using an organic acid (in particular, formic acid) as the reaction solvent is an epoch-making technique because this makes it possible to obtain the desired product with great ease and in high yield.

We claim:

1. A dihalogenothiocyanopyrimidine derivative of the formula

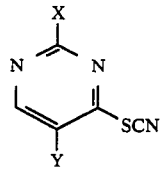

(I)

wherein X and Y are halogen atoms.

2. An agricultural and horticultural fungicidal composition comprising an effective amount of a dihalogenothiocyanopyrimidine derivative of the formula

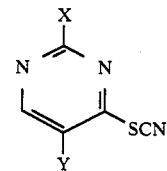

wherein X and Y are halogen atoms, in admixture with an inert carrier.

3. The composition of claim 2 wherein the effective amount is 0.1 to 90 percent by weight.

4. The composition of claim 2 wherein there is admixed an adjuvant.

* * * * *